US009913741B2

(12) United States Patent
Melsheimer et al.

(10) Patent No.: US 9,913,741 B2
(45) Date of Patent: Mar. 13, 2018

(54) CONTROL HANDLE FOR SELF-EXPANDABLE MEDICAL DEVICES

(75) Inventors: Jeffry S. Melsheimer, Springville, IN (US); Grant T. Hoffman, Bloomington, IN (US); Joseph E. Hughes, Batavia, OH (US); Gregory A. Frankland, Bloomington, IN (US); Tyler Bunch, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 641 days.

(21) Appl. No.: 13/542,137

(22) Filed: Jul. 5, 2012

(65) Prior Publication Data

US 2013/0013049 A1 Jan. 10, 2013

Related U.S. Application Data

(60) Provisional application No. 61/504,550, filed on Jul. 5, 2011.

(51) Int. Cl.
*A61F 2/06* (2013.01)
*A61F 2/95* (2013.01)
*A61F 2/966* (2013.01)

(52) U.S. Cl.
CPC ............... *A61F 2/95* (2013.01); *A61F 2/966* (2013.01); *A61F 2002/9517* (2013.01)

(58) Field of Classification Search
CPC ........ A61F 2002/011; A61F 2002/9517; A61F 2002/9665; A61F 2/84; A61F 2/95; A61F 2/962; A61F 2/966; A61B 1/00066; A61B 1/0052; A61B 1/00121; A61B 1/00858; G05G 9/047; A63F 2250/48; A63F 2250/481; A63F 2250/482; A63F 2250/483; A63F 2250/484; A63F 2250/485; A63F 2250/486
USPC ....... 623/1.11, 1.12; 606/108, 109, 110, 113, 606/114, 127, 191, 194, 198, 200; D24/144, 145, 147
See application file for complete search history.

(56) References Cited

U.S. PATENT DOCUMENTS

| 5,391,172 | A | 2/1995 | Williams et al. |
| 5,807,342 | A * | 9/1998 | Musgrave ............. A61M 25/02 128/DIG. 26 |
| 5,891,154 | A | 4/1999 | Loeffler |
| 6,146,415 | A | 11/2000 | Fitz |
| 6,190,360 | B1 | 2/2001 | Iancea et al. |
| 6,395,017 | B1 | 5/2002 | Dwyer et al. |
| 6,673,101 | B1 * | 1/2004 | Fitzgerald ................. A61F 2/95 604/161 |

(Continued)

OTHER PUBLICATIONS

"Adjacent." Merriam-Webster.com Merriam-Webster,n.d. Web. Apr. 30, 2016.*

*Primary Examiner* — Katrina Stransky
*Assistant Examiner* — Kankindi Rwego
(74) *Attorney, Agent, or Firm* — Brinks Gilson & Lione

(57) ABSTRACT

A delivery system is provided for a self-expanding medical device. The delivery system has a handle assembly with a housing. The housing has a slot with a deployment knob extending therethrough. The self-expanding medical device is deployed by restraining the housing of the handle assembly and pulling on the deployment knob. This causes an outer sheath to withdraw proximally from an inner catheter to release the self-expanding medical device from a space between the outer sheath and inner catheter.

20 Claims, 12 Drawing Sheets

(56) References Cited

U.S. PATENT DOCUMENTS

| | | | |
|---|---|---|---|
| 6,695,862 B2 | 2/2004 | Cox et al. | |
| 6,786,918 B1 | 9/2004 | Krivoruchko et al. | |
| 6,860,898 B2 | 3/2005 | Stack et al. | |
| 6,866,669 B2 | 3/2005 | Buzzard et al. | |
| 6,939,352 B2 | 9/2005 | Buzzard et al. | |
| 7,238,197 B2 | 7/2007 | Sequin et al. | |
| 7,381,216 B2 * | 6/2008 | Buzzard | A61F 2/95 606/108 |
| 7,491,224 B2 | 2/2009 | Cox et al. | |
| 7,837,725 B2 | 11/2010 | Fitzgerald et al. | |
| 8,414,501 B2 * | 4/2013 | Hanley et al. | 600/549 |
| 8,585,747 B2 * | 11/2013 | Andreas | A61F 2/95 623/1.11 |
| 2003/0004534 A1 * | 1/2003 | George | A61B 17/12099 606/191 |
| 2006/0263145 A1 * | 11/2006 | Pal | A61F 2/95 403/1 |
| 2007/0073389 A1 * | 3/2007 | Bolduc | A61B 17/064 623/1.36 |
| 2007/0112334 A1 * | 5/2007 | Porter | A61F 2/0077 604/539 |
| 2007/0156225 A1 | 7/2007 | George et al. | |
| 2007/0230167 A1 * | 10/2007 | McMahon | A61B 1/303 362/157 |
| 2008/0097572 A1 | 4/2008 | Sheldon et al. | |
| 2008/0269865 A1 | 10/2008 | Snot et al. | |
| 2009/0030496 A1 | 1/2009 | Kaufmann et al. | |
| 2010/0191326 A1 * | 7/2010 | Alkhatib | A61F 2/013 623/2.11 |
| 2011/0137402 A1 * | 6/2011 | Dorn | A61F 2/95 623/1.12 |

* cited by examiner

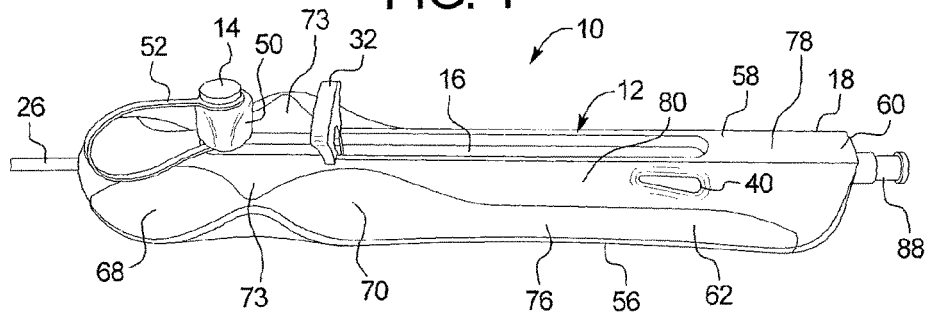
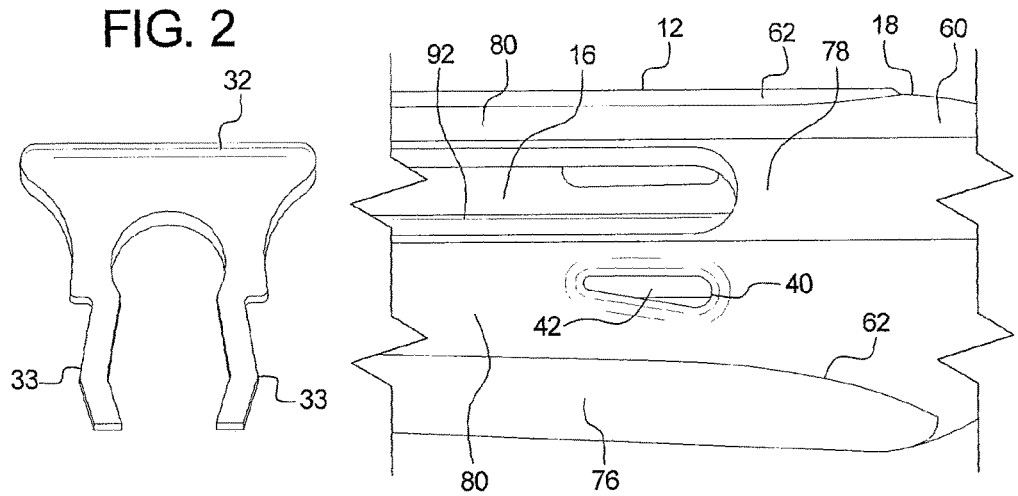
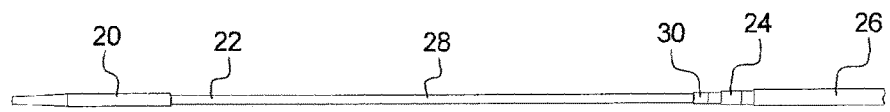

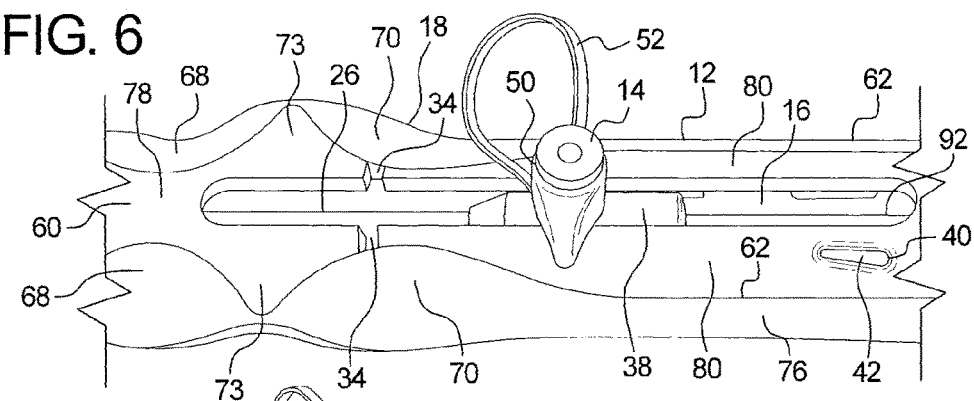

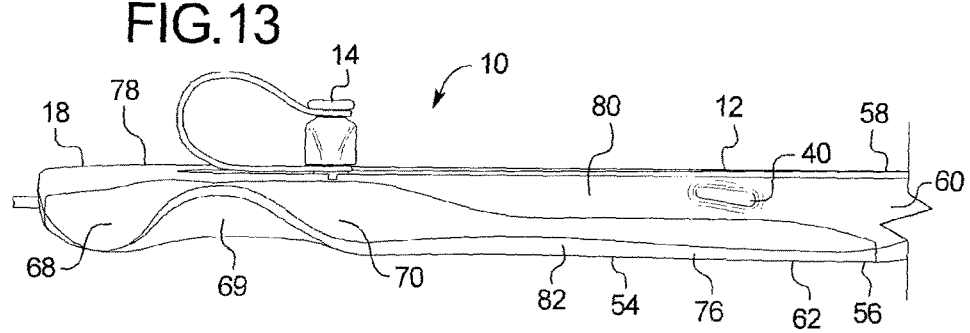
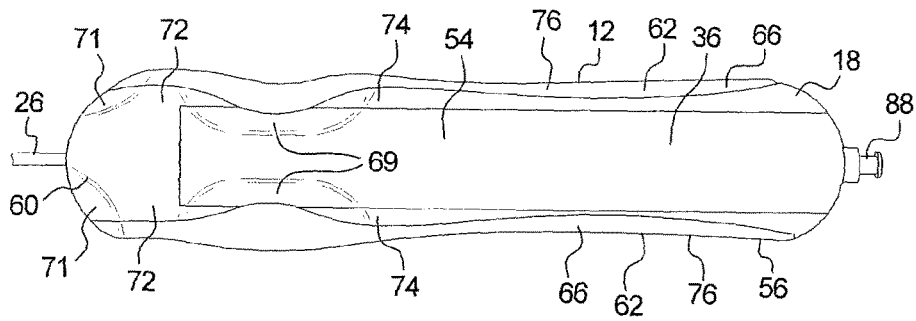
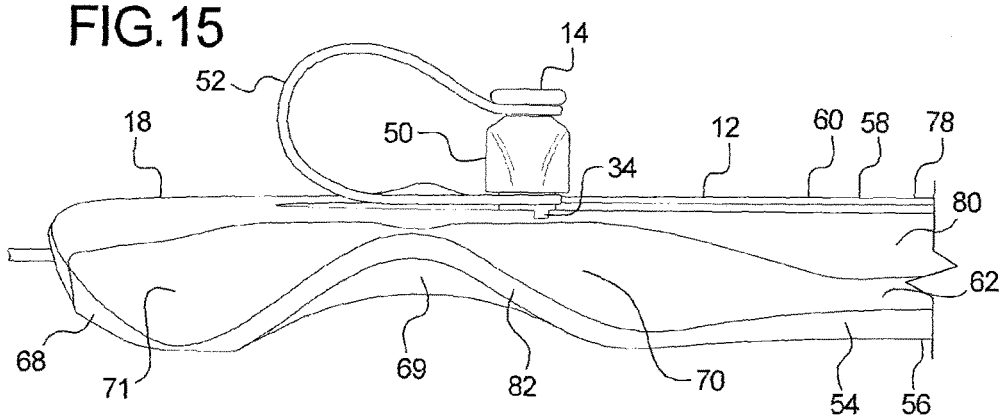
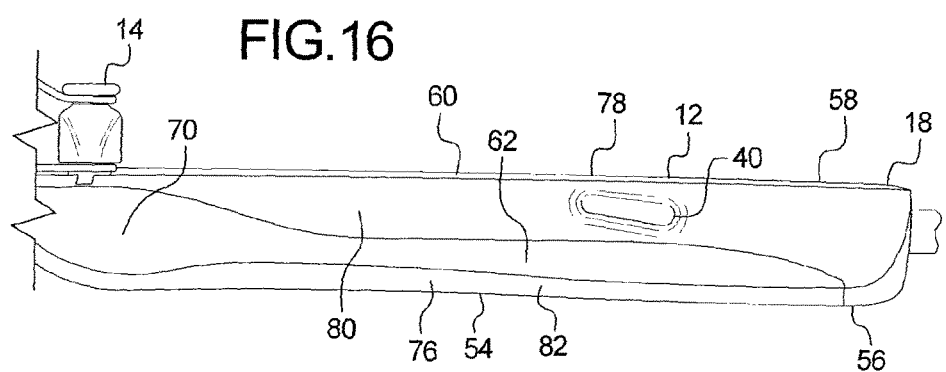

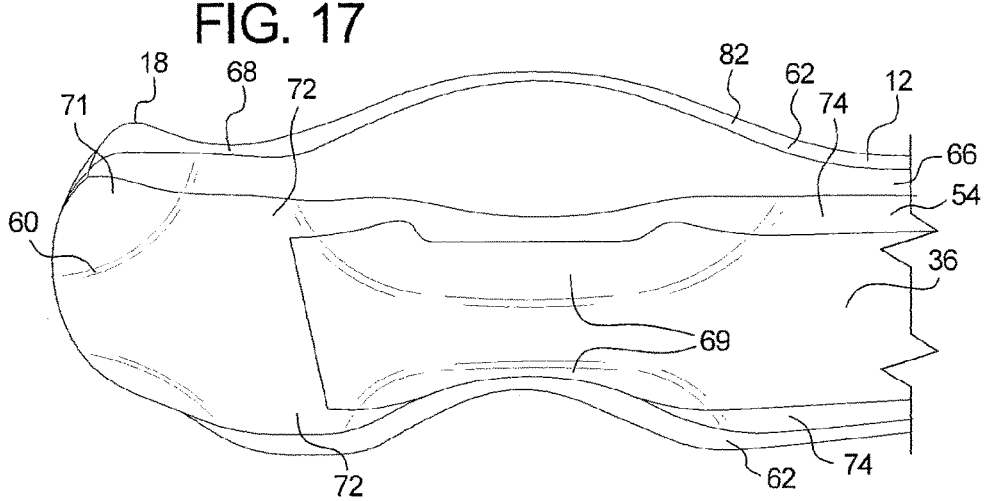
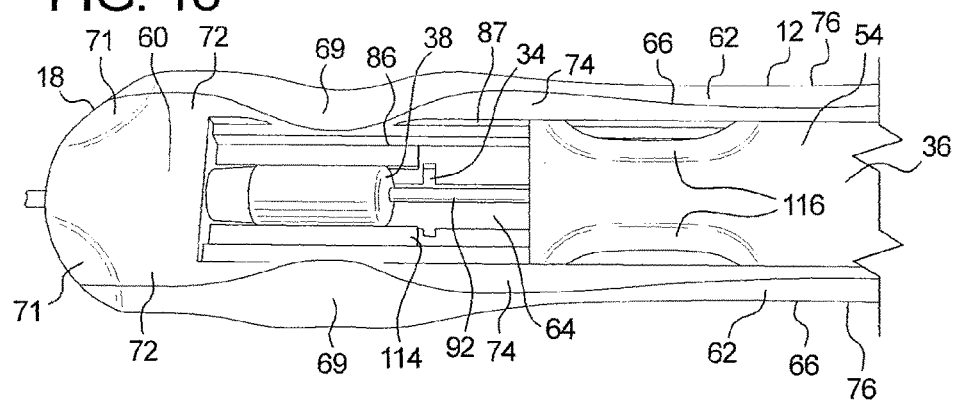
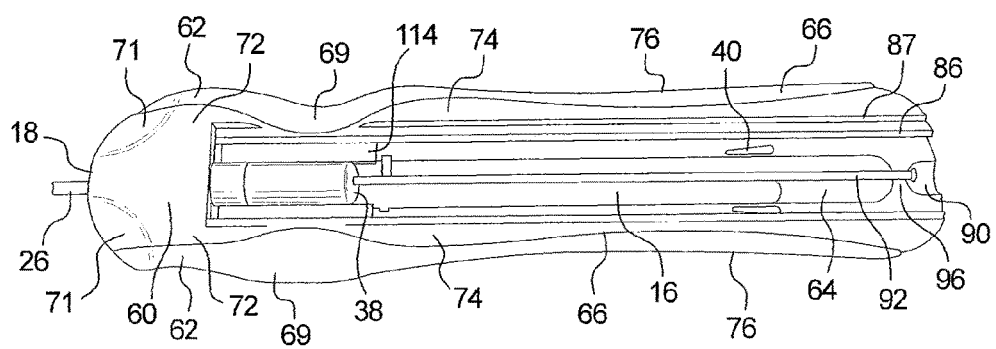
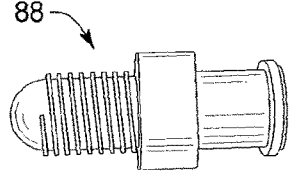

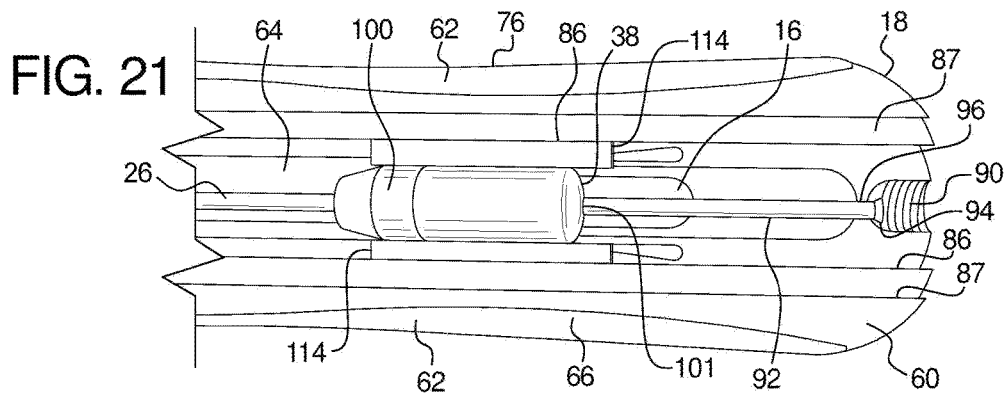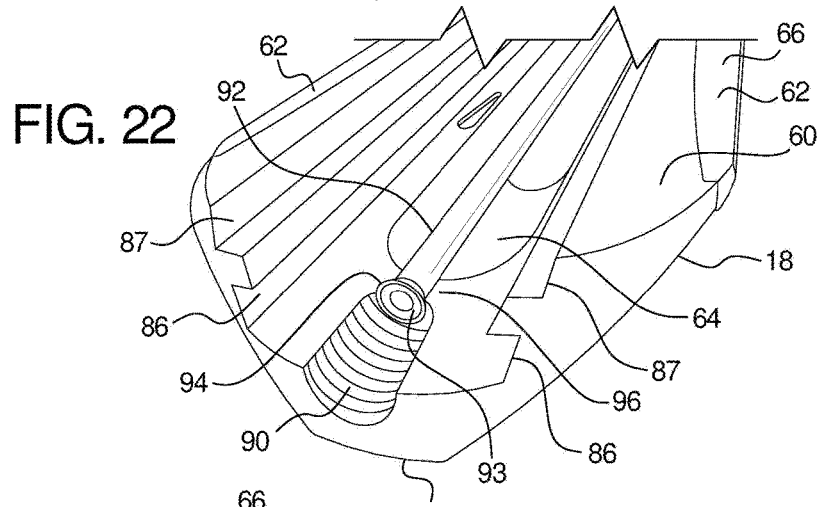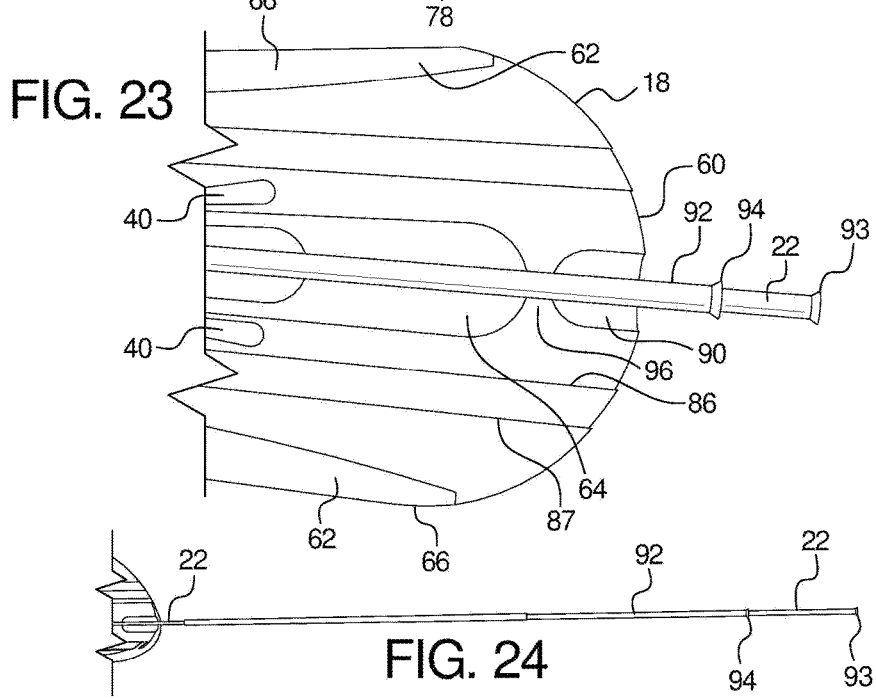

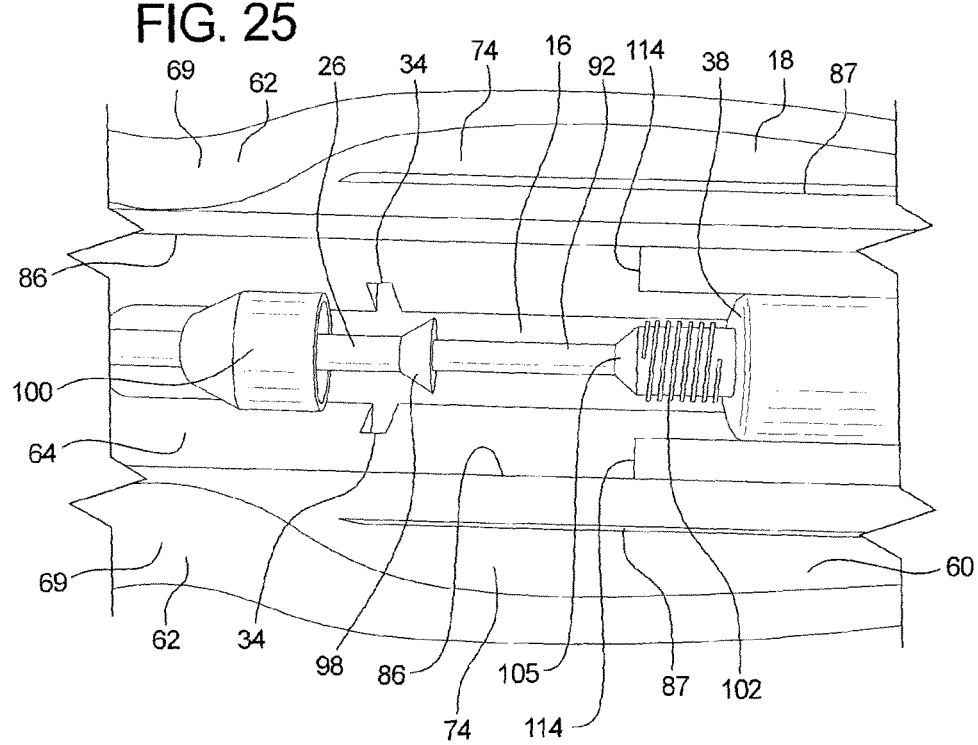
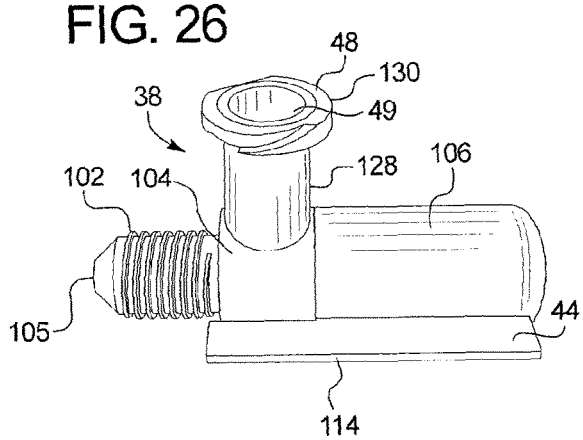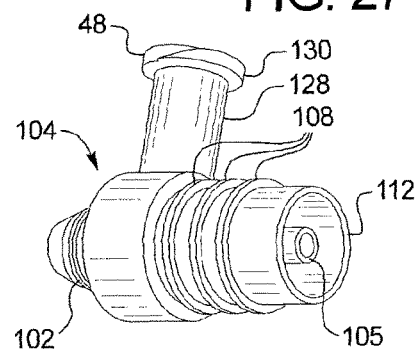
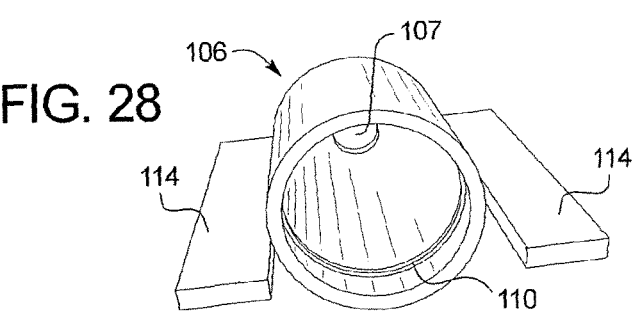

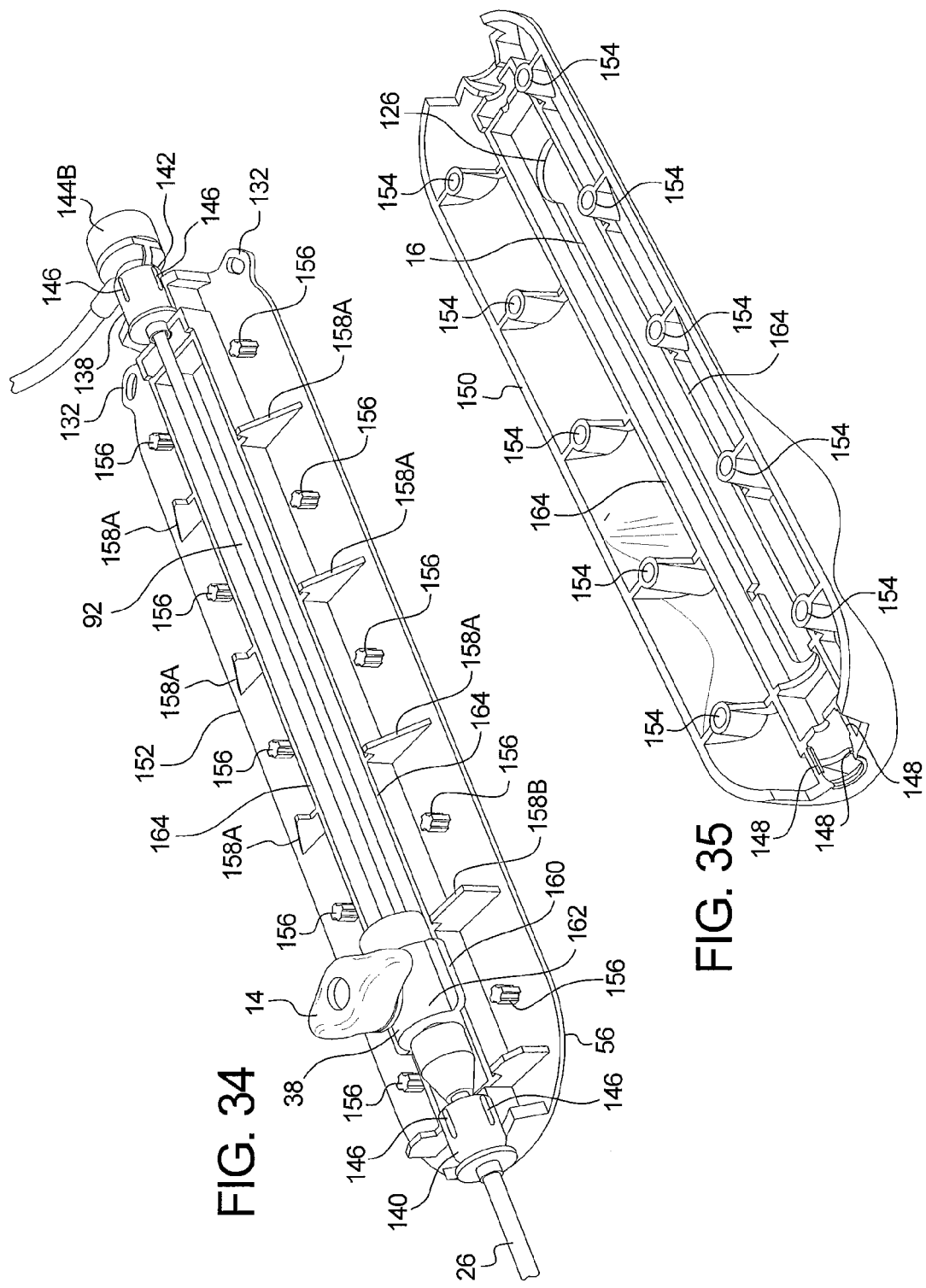

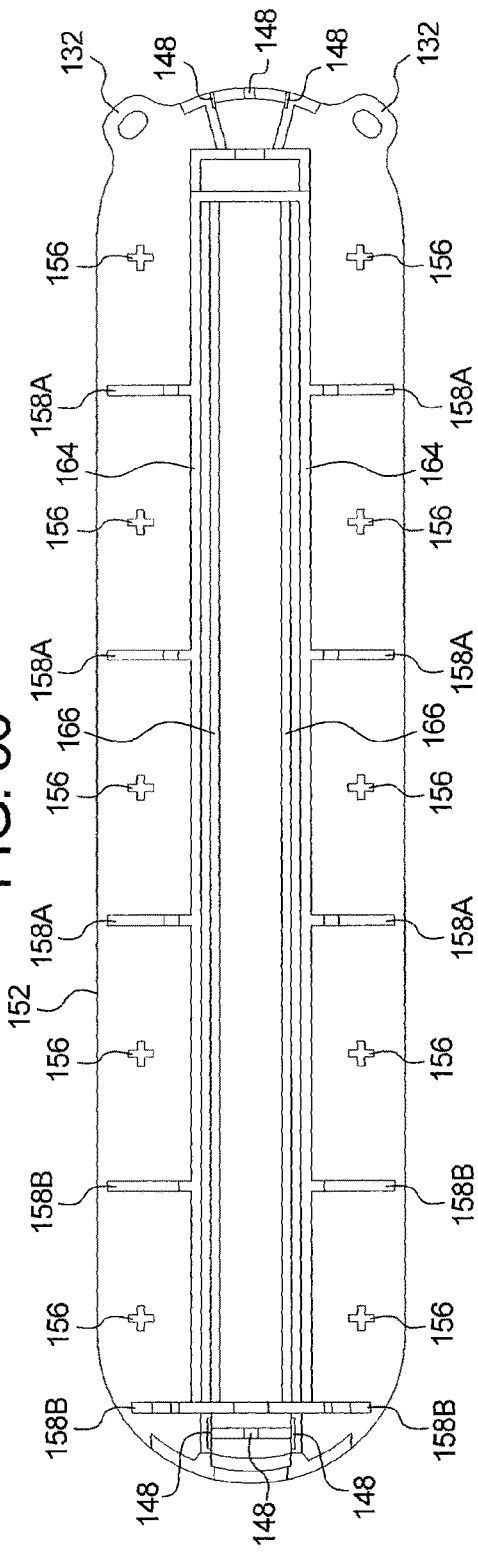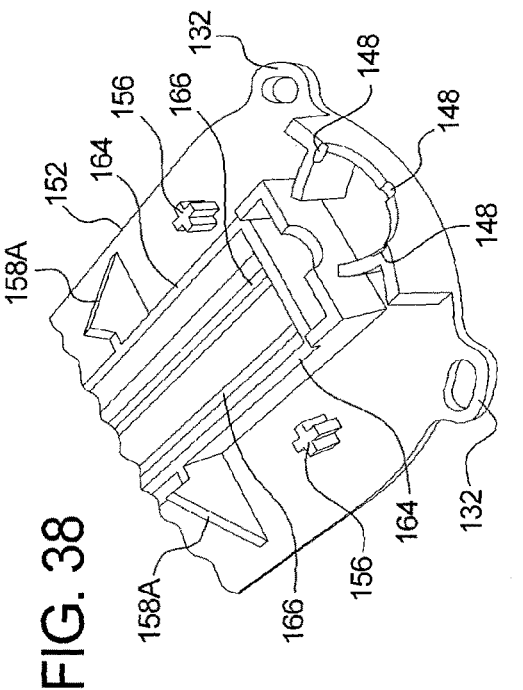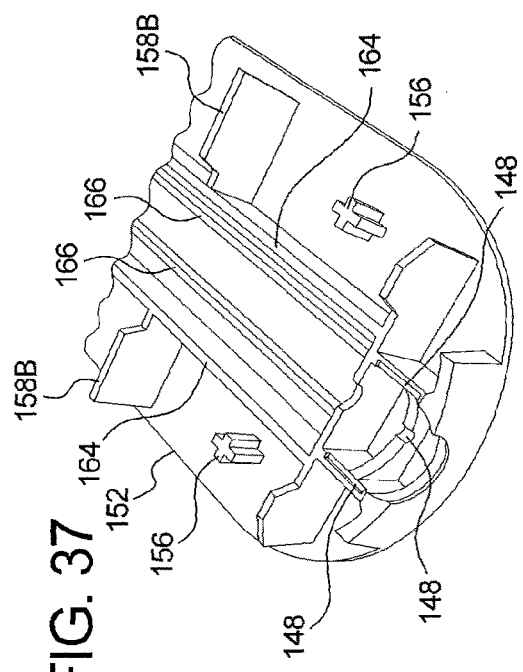

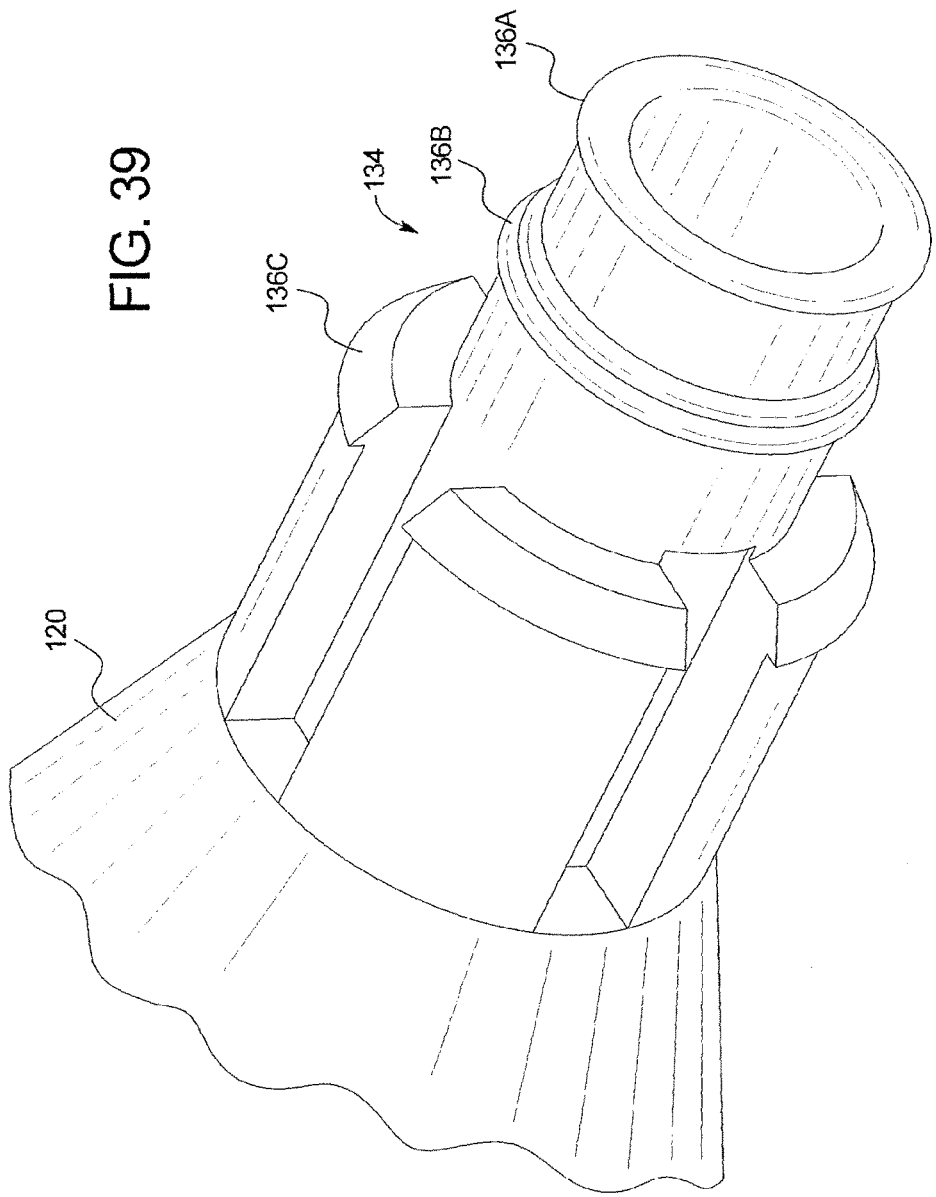

CONTROL HANDLE FOR SELF-EXPANDABLE MEDICAL DEVICES

This application claims priority to U.S. Provisional Application No. 61/504,550, filed Jul. 5, 2011, which is hereby incorporated by reference herein.

BACKGROUND

The present invention relates generally to medical devices and more particularly to delivery systems for self-expandable medical devices.

Self-expanding medical devices are used by physicians to treat numerous conditions using minimally invasive procedures. Examples of self-expanding medical devices include stents, stent-grafts, filters, valves, etc. Typically, self-expanding medical devices are made from an elastic structure that may be compressed into a low profile state that can be passed through vessels in a patient with minimal trauma. Once at the desired treatment site, the self-expanding medical device is released and self-expands like a spring until it contacts a tissue wall which prevents further expansion. Common materials that are used in self-expanding medical devices include nitinol and stainless steel, although other materials are also possible.

One type of self-expanding medical device that has become especially common is intraluminal stents. Stents are used to treat various organs, such as the vascular system, colon, biliary tract, urinary tract, esophagus, trachea and the like. For example, stents are commonly used to treat blockages, occlusions, narrowing ailments and other similar problems that restrict flow through a passageway. One area where stents are commonly used for treatment involves implanting an endovascular stent into the vascular system in order to improve or maintain blood flow through narrowed arteries. However, stents are also used in other treatments as well, such as the treatment of aneurysms. Stents have been shown to be useful in treating various vessels throughout the vascular system, including both coronary vessels and peripheral vessels (e.g., carotid, brachial, renal, iliac and femoral). In addition, stents have been used in other body vessels as well, such as the digestive tract.

The use of stents in coronary and peripheral vessels has drawn particular attention from the medical community because of the growing number of people each year that suffer from vasculature problems associated with stenosis (i.e., narrowing of a vessel). This has led to an increased demand for medical procedures to treat such problems. The widespread frequency of heart problems and other vasculature problems may be due to a number of societal changes, including the tendency of people to exercise less and the prevalence of unhealthy diets, in conjunction with the fact that people generally have longer life spans now than previous generations. Stents have become a popular alternative for treating vascular stenosis because stenting procedures are considerably less invasive than conventional procedures. For example, stenosis of the coronary arteries was traditionally treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient. Vascular stents are also being more widely used to treat many different peripheral arteries due to the minimally invasive nature of stenting procedures. To address the growing demand for minimally invasive medical procedures for the treatment of coronary arteries, peripheral arteries and other passageway problems, the medical community has begun to turn away from conventional invasive procedures like bypass surgery and increasingly the treatment of choice now involves a variety of stenting procedures.

Many different types of stents and stenting procedures are possible. In general, however, stents are typically designed as tubular support structures that may be inserted percutaneously and transluminally through a body passageway. Traditionally, stents are made from a metal or other synthetic material with a series of radial openings extending through the support structure of the stent to facilitate compression and expansion of the stent. Although stents may be made from many types of materials, including non-metallic materials, common examples of metallic materials that may be used to make stents include stainless steel, nitinol, cobalt-chrome alloys, amorphous metals, tantalum, platinum, gold and titanium. Typically, stents are implanted within a passageway by positioning the stent within the area to be treated and then expanding the stent from a compressed diameter to an expanded diameter. The ability of the stent to expand from a compressed diameter makes it possible to thread the stent to the area to be treated through various narrow body passageways while the stent is in the compressed diameter. Once the stent has been positioned and expanded at the area to be treated, the tubular support structure of the stent contacts and radially supports the inner wall of the passageway. As a result, the implanted stent mechanically prevents the passageway from narrowing and keeps the passageway open to facilitate fluid flow through the passageway.

Stents can generally be characterized as either balloon-expandable or self-expanding. Traditionally, balloon-expandable stents have been used most often in coronary vessels than in peripheral vessels because of the deformable nature of these stents. One reason for this is that peripheral vessels tend to experience frequent traumas from external sources (e.g., impacts to a person's arms, legs, etc.) which are transmitted through the body's tissues to the vessel. In the case of peripheral vessels, there is an increased risk that an external trauma could cause a balloon-expandable stent to plastically deform in unexpected ways with potentially severe and/or catastrophic results. However, in the case of coronary vessels, this risk is minimal since coronary vessels rarely experience traumas transmitted from external sources.

Self-expanding stents are increasingly used and accepted by physicians for treating a variety of ailments. Self-expanding stents are usually made of shape memory materials or other elastic materials that act like a spring. Typical metals used in this type of stent include nitinol and 304 stainless steel. A common procedure for implanting a self-expanding stent involves a two-step process. First, the narrowed vessel portion to be treated is dilated with a balloon but without a stent mounted on the balloon. Second, a stent is implanted into the dilated vessel portion. To facilitate stent implantation, the stent is installed on the end of an inner catheter in a compressed, small diameter state and is usually retained in the small diameter by inserting the stent into an outer sheath at the end of the catheter. The stent is then guided to the balloon-dilated portion and is released from the inner catheter by pulling the outer sheath away from the stent. Once released from the outer sheath, the stent radially springs outward to an expanded diameter until the stent contacts and presses against the vessel wall. Traditionally, self-expanding stents have been more commonly used in peripheral vessels than in coronary vessels due to the shape memory characteristic of the metals that are used in these stents. One advantage of self-expanding stents for peripheral vessels is that traumas from external sources do not permanently deform the stent. Instead, the stent may temporarily deform during an unusually harsh trauma but will spring back to its expanded state once the trauma is relieved. Self-expanding stents, however, are often considered to be less preferred for coronary vessels as compared to balloon-expandable stents. One reason for this is that balloon-expandable stents can be precisely sized to a particular vessel diameter and shape since the ductile metal that is used can be plastically deformed to a desired size and shape. In contrast, self-expanding stents are designed with a particular expansible range. Thus, after being implanted, self-expanding stents continue to exert pressure against the vessel wall.

Commonly, delivery systems for self-expanding medical devices have a handle arrangement that remains outside of the patient's body during the deployment procedure. One portion of the handle is typically connected to an inner catheter upon which the self-expanding medical device is mounted, and another portion of the handle is typically connected to an outer sheath which restrains the self-expanding medical device in the compressed state. When the distal end of the delivery system is positioned within the patient's body at the intended treatment site, the physician actuates the handle by moving the two portions relative to each other so that the outer sheath is withdrawn from the self-expanding medical device and inner catheter. As a result, the self-expanding medical device expands outward away from the inner catheter. The handle may then be pulled by the physician to withdraw the inner catheter and outer sheath from the patient's body, while leaving the self-expanding medical device implanted in the body.

Precise placement of self-expanding medical devices is a concern in most medical procedures. However, precise placement can be more difficult with certain delivery systems due to their design, shape and other factors. Precise placement of self-expanding medical devices is generally a function of the relative movement and placement between the delivery system handle and the patient's body, and the relative movement between the portions of the handle connected to the inner catheter and outer sheath during deployment. A lack of control over any part of this system can result in inaccurate placement of a self-expanding medical device, and thus, less than desirable treatment of the medical condition being treated.

Accordingly, the inventor believes it would be desirable to provide a new delivery system for self-expanding medical devices.

SUMMARY

A delivery system is described which may be used to deploy a self-expanding medical device. The self-expanding medical device is restrained in a compressed state between the distal end of an inner catheter and the distal end of an outer sheath. When the self-expanding medical device has been positioned at the desired treatment site, the physician pulls on the deployment knob of a handle assembly and restrains a housing of the handle assembly relative to the patient. This causes the outer sheath to withdraw from the self-expanding medical device and permits the self-expanding medical device to expand away from the inner catheter. The invention may also include any other aspect described below in the written description or in the attached drawings and any combinations thereof.

BRIEF DESCRIPTION OF SEVERAL VIEWS OF THE DRAWINGS

The invention may be more fully understood by reading the following description in conjunction with the drawings, in which:

FIG. 1 is a top side view of a delivery system for a self-expanding medical device;

FIG. 2 is a side view of the lock;

FIG. 3 is a top view of a proximal portion of the handle assembly;

FIG. 4 is a side view of the distal portion of the delivery system in the initial state;

FIG. 5 is a side view of the distal portion of the delivery system in the released state;

FIG. 6 is a top view of the handle assembly, showing the deployment knob partially moved proximally;

FIG. 7 is a top view of the handle assembly, showing the deployment knob moved proximally so that the indicator window shows the color red on the distal side and the color green on the proximal side;

FIG. 8 is a top view of the handle assembly, showing the deployment knob moved proximally farther so that the indicator window shows only the color red;

FIG. 9 is a top view of the handle assembly, showing the deployment knob moved proximally against the end of the slot;

FIG. 13 is a side view of the handle assembly;

FIG. 14 is a bottom view of the handle assembly;

FIG. 15 is a side view of a distal portion of the handle assembly;

FIG. 16 is a side view of a proximal portion of the handle assembly;

FIG. 17 is a bottom side view of a distal portion of the handle assembly;

FIG. 18 is a bottom view of a distal portion of the handle assembly, showing the bottom cover partially removed;

FIG. 19 is a bottom view of the handle assembly, showing the bottom cover removed;

FIG. 20 is a side view of threaded luer fitting;

FIG. 21 is a bottom view of a proximal portion of the handle assembly, showing the bottom cover removed;

FIG. 22 is an end bottom view of the handle assembly, showing the bottom cover removed;

FIG. 23 is a bottom view of a proximal portion of the handle assembly, showing the inner catheter and cannula;

FIG. 24 is a side view of the inner catheter and cannula;

FIG. 25 is a bottom view of a portion of the handle assembly, showing the connection of the outer sheath to the slide;

FIG. 26 is a side top view of the slide;

FIG. 27 is a side end view of the slide body;

FIG. 28 is a front view of the slide cap;

FIG. 34 is a perspective view of the inside of a bottom housing;

FIG. 35 is a perspective view of the inside of a top housing;

FIG. 36 is a top view of the inside of the bottom housing;

FIG. 37 is a close-up perspective view of the distal end of the bottom housing;

FIG. 38 is a close-up perspective view of the proximal end of the bottom housing; and FIG. 39 is a close-up perspective view of a connector.

DETAILED DESCRIPTION

Figure 10:
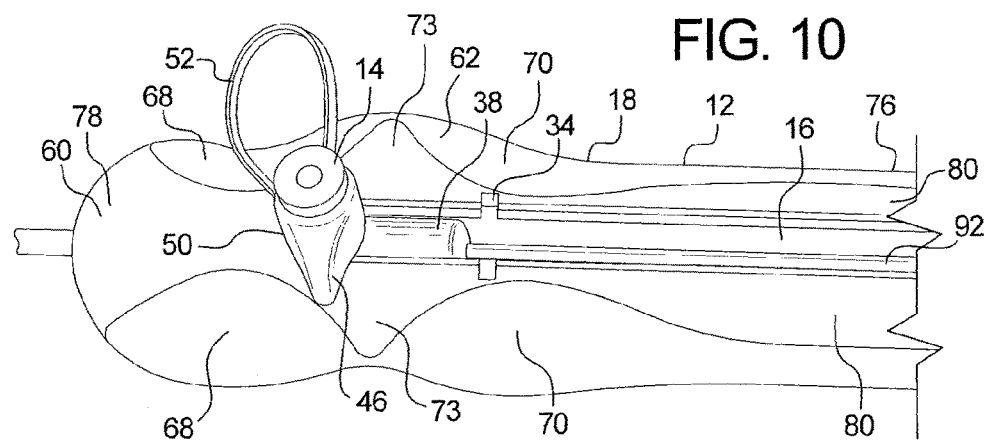
FIG. 10 is a top view of a distal portion of the handle assembly.

Referring now to the figures, and particularly to FIG. 1, a delivery system 10 for a self-expanding medical device, such as a stent, is shown. The delivery system 10 is shown in FIG. 1 in its initial state as it would be provided to a physician. The distal end of the delivery system 10 is shown in FIGS. 4 and 5. FIG. 4 shows the distal end of the delivery system 10 in the initial state, which corresponds to the position of the deployment knob 14 shown in FIGS. 1 and 10-11. As shown, in this position the deployment knob 14 is positioned toward the distal end of the slot 16 in the housing 18 of the handle assembly 12. FIG. 5 shows the distal end of the delivery system 10 in the released state, which permits a stent to self-expand and release itself away from the delivery system 10. The released state shown in FIG. 5 corresponds to the position of the deployment knob 14 shown in FIG. 9, where the deployment knob 14 has been moved toward the proximal end of the slot 16 in the housing 18 of the handle assembly 12.

As shown in FIGS. 4 and 5, the distal end of the delivery system 10 has a dilator tip 20 attached to an inner catheter 22. The inner catheter 22 is provided with a metal band 24 proximally from the dilator tip 20. The metal band 24 provides a stepped surface 24 that functions as a retention surface 24 to longitudinally restrain the stent during deployment so that the stent remains fixed in place relative to the inner catheter 22 and does not move with the outer sheath 26. In the initial state, the stent is mounted on the inner catheter 22 in the stent receiving region 28 between the dilator tip 20 and the retention surface 24. The inner catheter 22 may also be provided with a second restraint member 30 which may have a protrusion that extends partially through the structure of the stent to restrain the stent from moving distally during deployment away from the retention surface 24. As shown in FIG. 4, in the initial state, the distal end of the outer sheath 26 is positioned adjacent to or over the dilator tip 20 so that the stent remains radially restrained by the outer sheath 26 in a compressed state between the outer sheath 26 and the inner catheter 22. As described further below, the inner catheter 22 is connected to the housing 18, and the outer sheath 26 is connected to the deployment knob 14. Therefore, in order to release a self-expanding medical device from the delivery system, a physician holds the housing 18 to restrain it relative to the patient's body, and pulls proximally on the deployment knob 14 to withdraw the outer sheath 26 away from the dilator tip 20.

Figure 29:
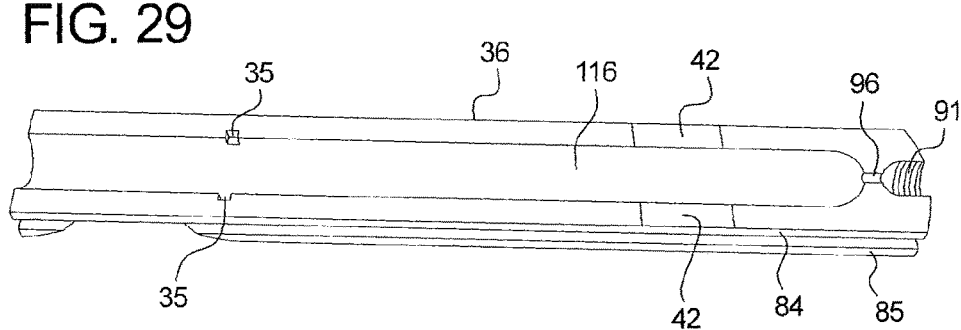
FIG. 29 is a top view of the bottom cover.

As shown in FIGS. 1-2, the delivery system 10 is provided with a deployment lock 32 to prevent premature deployment of the delivery system 10. As described above, in the initial state, the deployment knob 14 is positioned adjacent the distal end of the slot 16 in the housing 18. The lock 32 has two prongs 33 that snap into a pair of recesses 34 in the housing 18, as shown in FIG. 10, and another pair of recesses 35 in the bottom cover 36, as shown in FIG. 29. Thus, the lock 32 prevents the slide 38 from moving proximally until the lock 32 is removed, since the prongs 33 block the slide 38 from moving proximally. Preferably, the lock 32 is no higher than the deployment knob 14 when it is installed.

As shown in FIG. 3, the housing 18 is provided with indicator windows 40 that extend through the housing 18. As shown in FIG. 29, the inner surface of the bottom cover 36 is provided with colored portions 42, such as green, that are aligned with the indicator windows 40 so that in the initial state a physician sees the green color 42 through the indicator windows 40. As shown in FIGS. 6-9, the delivery system 10 is actuated by pulling on the deployment knob 14 so that the deployment knob 14 moves proximally through the slot 16 in the housing 18. As shown in FIG. 6, when the deployment knob 14 is partially moved proximally, the physician still sees the green color 42 through the indicator windows 40. This position corresponds to the outer sheath 26 being partially withdrawn from the inner catheter 22 so that the stent is partially released. As shown in FIG. 7, when the deployment knob 14 reaches a location toward the proximal end of the slot 16, differently colored portions 44 on the slide 38, such as red, begin the pass by the indicator windows 40 so that the physician sees a red portion 44 on the distal side of the indicator window 40 and a green portion 42 on the proximal side of the indicator window 40. As shown in FIG. 8, as the deployment knob 14 is moved proximally further, the red portion 44 of the slide 38 completely obstructs the green portion 42 of the bottom cover 36. Thus, the physician now only sees red 44 through the indicator windows 40, which indicates that the outer sheath 26 has been fully withdrawn from the stent, thereby releasing it to self-expand. Alternatively, the green and red portions 42, 44 may be positioned to indicate other conditions, such as a "point of no return" in which the stent can no longer be repositioned prior to full deployment. As shown in FIG. 9, the slot 16 may allow the deployment knob 14 to move proximally slightly farther than the fully released position, where the proximal end of the slot 16 provides a solid stop for the deployment knob 14.

Figure 11:
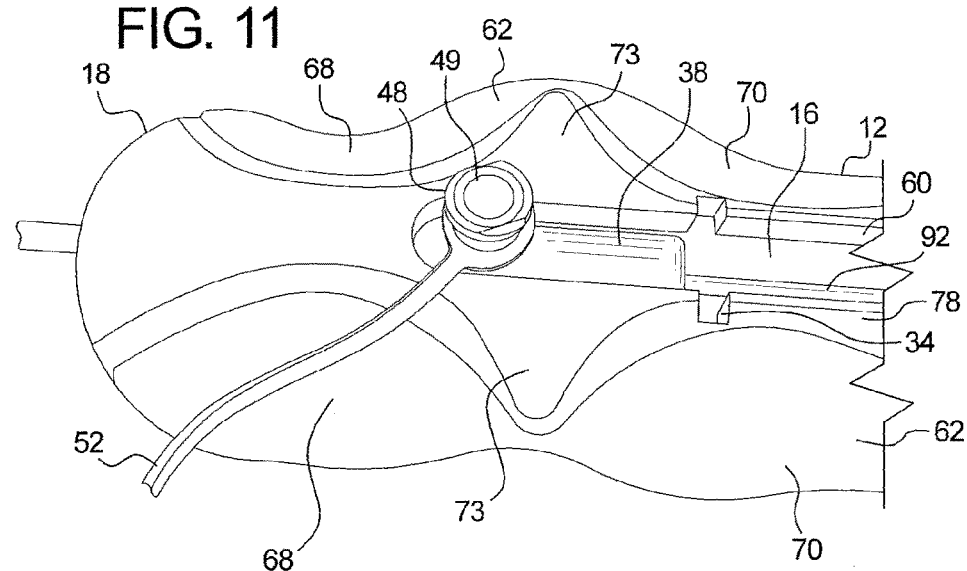
FIG. 11 is a top view of a distal portion of the handle assembly, showing the cap removed from the luer fitting.
Figure 12A:
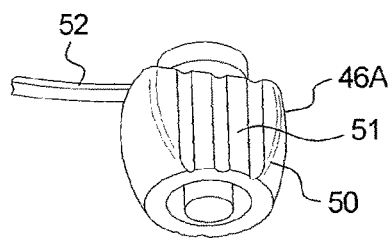
FIG. 12A is a side view of one cap.
Figure 12B:
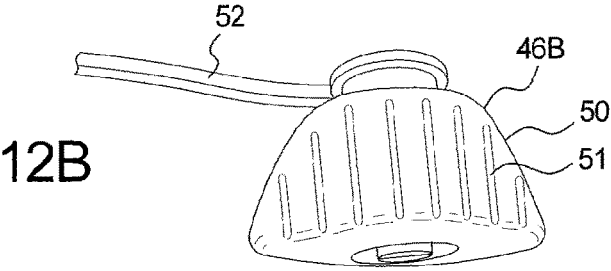
FIG. 12B is a side view of another cap.

As shown in FIGS. 10-12B, the deployment knob 14 is provided with a cap 46 that threads onto a luer fitting 48 connected to the slide 38. As shown in FIGS. 12A-12B, the cap 46 preferably has a generally flat surface 50 that is perpendicular to the axis of the handle assembly 12. The flat surface 50 is preferably provided with a gripping texture 51 so that the cap 46 can be comfortably gripped to pull the slide 38 along the slot 16. The threaded connection between the cap 46 and the luer fitting 48 may be a quarter turn connection so that the threaded connection starts with the flat surface 50 of the cap 46 being parallel to the axis of the handle assembly 12 and physically stops when the flat surface 50 reaches the perpendicular orientation. As shown in FIG. 11, the cap 46 may be removed to flush the delivery system 10 prior to use. The port 49 in the luer fitting 48 is in fluid communication with the annular space between the inner catheter 22 and the outer sheath 26 so that the flushing fluid flows out the distal end of the outer sheath 26 through the compressed stent restrained between the inner catheter 22 and the outer sheath 26. The cap 46 may also be provided with a retention strap 52 attached to the cap 46 and the luer fitting 48 to prevent the cap 46 from being inadvertently misplaced.

As shown in FIGS. 13-14, the handle assembly 12 has a generally flat bottom surface 54. The width of the bottom surface 54 is relatively wide relative to the height of the handle assembly 12 between the bottom side 56 and the top side 58. For example, a ratio between the width of the bottom flat surface 54 and the height of the handle assembly 12 is preferably about 2.5:1 to about 3.5:1, or more preferably about 2.85:1 to about 3.2:1. A ratio of about 3:1 may also be desirable. It is the inventor's believe that this ratio provides a comfortable fit within a physician's hand. Moreover, the wide bottom flat surface 54 allows the physician to firmly immobilize the handle assembly 12 against a patient's bed or against the patient's body during the treatment procedure. This provides more accuracy during deployment by providing improved stability for the position of the handle assembly 12. The described aspect ratio, however, is not limited by the length of the delivery system 10 since the length of the delivery system 10 may be adjusted to accommodate the length of the self-expanding medical device being deployed.

The housing 18 preferably has a rigid body structure 60 with a soft elastomer 62 along the opposing edge side surfaces of the housing 18. Thus, the slot 16 extends through the top side 58 of the rigid body structure 60 to an internal longitudinal opening 64 as shown in FIG. 19. The soft elastomer 62 may be made from various materials and preferably has a Shore A hardness of about 40 to about 87. Preferably, a portion 66 of the soft elastomer 62 extends along the flat bottom surface 54 of the housing 18 to provide improved grip between the handle assembly 12 and the surface that the housing 18 is restrained against, e.g., a patient's bed or body. Alternatively, a gripping texture may be provided along the flat bottom surface 54, such as raised or recessed ribs or the like. A series of finger recesses 68, 69, 70, 71 are also provided in the soft elastomer 62 to provide a better grip by a physician. As shown in FIGS. 10 and 15, two opposing first finger recesses 68 may be provided in the soft elastomer 62 along the top side 58 of the housing 18 near the distal end of the housing 18. Preferably, the first finger recesses 68 are positioned distally of the deployment knob 14 when the knob 14 is adjacent the distal end of the slot 16. As shown in FIGS. 15 and 17, two opposing second finger recesses 69 may also be provided in the soft elastomer 62 along the bottom side 56 of the housing 18. Preferably, the second finger recesses 69 are positioned proximally adjacent the first finger recesses 68. As shown in FIGS. 10 and 15, two opposing third finger recesses 70 may also be provided in the soft elastomer 62 along the top side 58 of the housing 18. Preferably, the third finger recesses 70 are positioned proximally adjacent the second finger recesses 69. As shown in FIGS. 10 and 14, first and third portions 72, 74 of the rigid body structure 60 extends under the soft elastomer 62 of the first and third finger recesses 68, 70, respectively, to provide support for the first and third finger recesses 68, 70. Similarly, second portions 73 of the rigid body structure 60 extend under the soft elastomer 62 of the second finger recesses 69 to support the second finger recesses 69. As shown in FIG. 18, fourth finger recesses 71 may be partially formed into the bottom side of the rigid body structure 60 and into the bottom portion 66 of the soft elastomer 62. The fourth finger recesses 71 may be positioned distal from the first finger recesses 68. Preferably, the first, second, third and fourth finger recesses 68, 69, 70, 71 do not change the overall aspect ratio of about 2.5:1 to about 3.5:1 described above.

As shown in FIGS. 1, 10 and 17, the portion of the soft elastomer 62 that forms the first, second and third finger recesses 68, 69, 70 is preferably wider than a portion 76 of the soft elastomer 62 extending proximally from the first, second and third finger recesses 68, 69, 70. The rigid body structure 60 of the housing 18 may have a central longitudinal flat portion 78 through which the slot 16 extends. Thus, the central portion 78 defines the height of the top side 58 of the housing 18. As shown in FIGS. 16 and 22, the top side 58 of the housing 18 has opposing sloped surfaces 80 that extend downward from the central portion 78 toward the soft elastomer 62 side surfaces 82. Preferably, the sloped surfaces 80 extend within an angular range of about 30° to about 60°. As shown in FIG. 16, indicator windows 40 may extend through the sloped surfaces 80. As shown in FIGS. 15-16, the side surfaces 82 of the soft elastomer 62 have a generally consistent height along more than 80% of the length of the housing 18. Preferably, the height of the soft elastomer 62 side surfaces 82 is about 0.125" to about 0.25", including the portion 76 of the soft elastomer 62 extending proximal from the finger recesses 68, 69, 70 and the portion extending along the finger recesses 68, 69, 70 as well as the wave-shaped portion of the second finger recesses 69.

As shown in FIGS. 18-19, the bottom cover 36 may be a separate piece from the housing 18. The separate bottom cover 36 may make assembly of the interior components of the handle assembly 12 easier. However, after the handle assembly 12 is assembled and the bottom cover 36 installed, the bottom cover 36 can be considered effectively a part of the housing 18. As shown in FIG. 31, the bottom cover 36 may have a first rail 84 and a second rail 85 that mate with a first longitudinal recess 86 and second longitudinal recess 87, respectively, in the housing 18 as shown in FIG. 22. Thus, the bottom cover 36 may be installed onto the housing 18 by sliding the first and second rails 84, 85 of the bottom cover 36 along the first and second recesses 86, 87 of the housing 18. This is accomplished by sliding the distal end of the bottom cover 36 into the proximal end of the housing 18 and sliding the bottom cover 36 distally along the housing 18. The engagement of the first rail 84 and first recess 86 prevents the bottom cover 36 from laterally separating from the housing 18. When the bottom cover 36 is fully installed into the bottom of the housing 18 so that the distal end of the bottom cover 36 abuts a distal portion of the housing 18, a threaded luer fitting 88, shown in FIG. 20, may be threaded into a first threaded portion 90 in the housing 18 and a second threaded portion 91 in the bottom cover 36, as shown FIGS. 1, 22 and 30. The first and second threaded portions 90, 91 of the housing 18 and the bottom cover 36 form a single threaded opening when the bottom cover 36 and housing 18 are mated together. As a result, the threaded connection of the luer fitting 88 with the first and second threaded portions 90, 91 locks the bottom cover 36 to the housing 18 to prevent the bottom cover 36 from sliding out of the housing 18. The luer fitting 88 may also have a longitudinal opening extending therethrough so that a guide wire can be passed through the luer fitting 88 and into the inner catheter 22. The luer fitting 88 also allows the inner catheter 22 to be flushed with fluid before using the delivery system 10.

As shown in FIGS. 18-19, the bottom cover 36 encloses the internal longitudinal opening 64 within the rigid body structure 60 of the housing 18. A stiff cannula 92, preferably made of metal, extends through the internal opening 64. As shown in FIGS. 23-24, the proximal end of the inner catheter 22 extends through the cannula 92. Since the cannula 92 principally provides a guide surface for the slide 38, the cannula 92 preferably extends only along the length of the handle assembly 12. As shown in FIGS. 23-24, the proximal ends of the cannula 92 and inner catheter 22 are flared 94, 93, respectively, which restrains the proximal ends of the cannula 92 and inner catheter 22 between the threaded luer fitting 88 and a hole 96 for the cannula 92 in the housing 18 and in the bottom cover 36.

As shown in FIG. 21, the cannula 92 extends through the slide 38 and the outer sheath 26. As shown in FIG. 25, the outer sheath 26 is attached to the slide 38 with a flared proximal end 98 that is restrained between a nut 100 and a distal threaded portion 102 of the slide 38. As shown in FIGS. 26-28, the slide 38 may be made of a slide body 104 and a slide cap 106 that are assembled together. The slide body 104 has a hole 105 extending therethrough to receive the cannula 92, and the slide cap 106 has a corresponding hole 107 extending through the proximal end of the cap 106. As shown in FIGS. 26-27, the slide body 104 as a distal threaded portion 102 for engaging the nut 100 and a luer fitting 48 that extends through the slot 16 in the housing 18 and receives the cap 46. The slide body 104 may also have one or more recesses 108 on the proximal side that are received by a raised ring 110 in the slide cap 106 to snap the slide body 104 and cap 106 together. At the proximal end, the slide body 104 may also have a recess 112 for an O-ring that seals the proximal end of the slide 38 against the cannula 92. This prevents flushing fluid injected into the luer fitting port 49 from escaping between the slide 38 and the cannula 92. The slide cap 106 traps the O-ring in the recess 112 of the slide body 104. The slide cap 106 may also be provided with indicator tabs 114 with the red colored portions 44. As shown in FIGS. 21 and 25, the indicator tabs 114 may slide within the first recesses 86 of the housing 18 and can be restrained between the first recesses 86 and the first rails 84 of the bottom cover 36.

Figure 30:
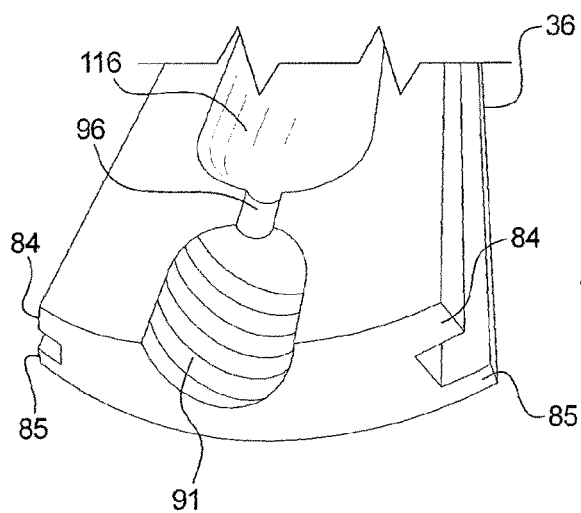
FIG. 30 is a top end view of the bottom cover.
Figure 31:
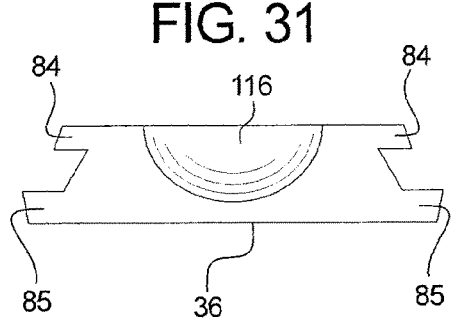
FIG. 31 is a front view of the bottom cover.
Figure 32:
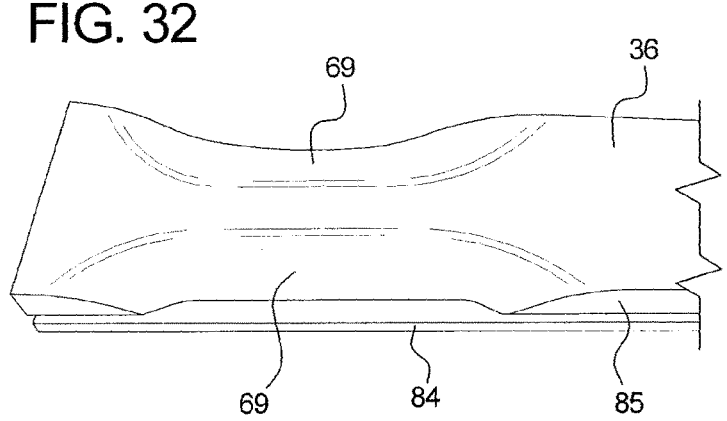
FIG. 32 is a side bottom view of a distal portion of the bottom cover.

As shown in FIGS. 29-31, the top of the bottom cover 36 may have a recess 116 that forms part of the internal opening 64 of the housing 18 to allow the slide 38 to move inside of the handle assembly 12. As shown in FIG. 32, the second finger recesses 69 may be formed partially into the bottom of the bottom cover 36. Preferably, the bottom cover 36 is made from a rigid material like the rigid body structure 60 of the housing 18.

Figure 33:
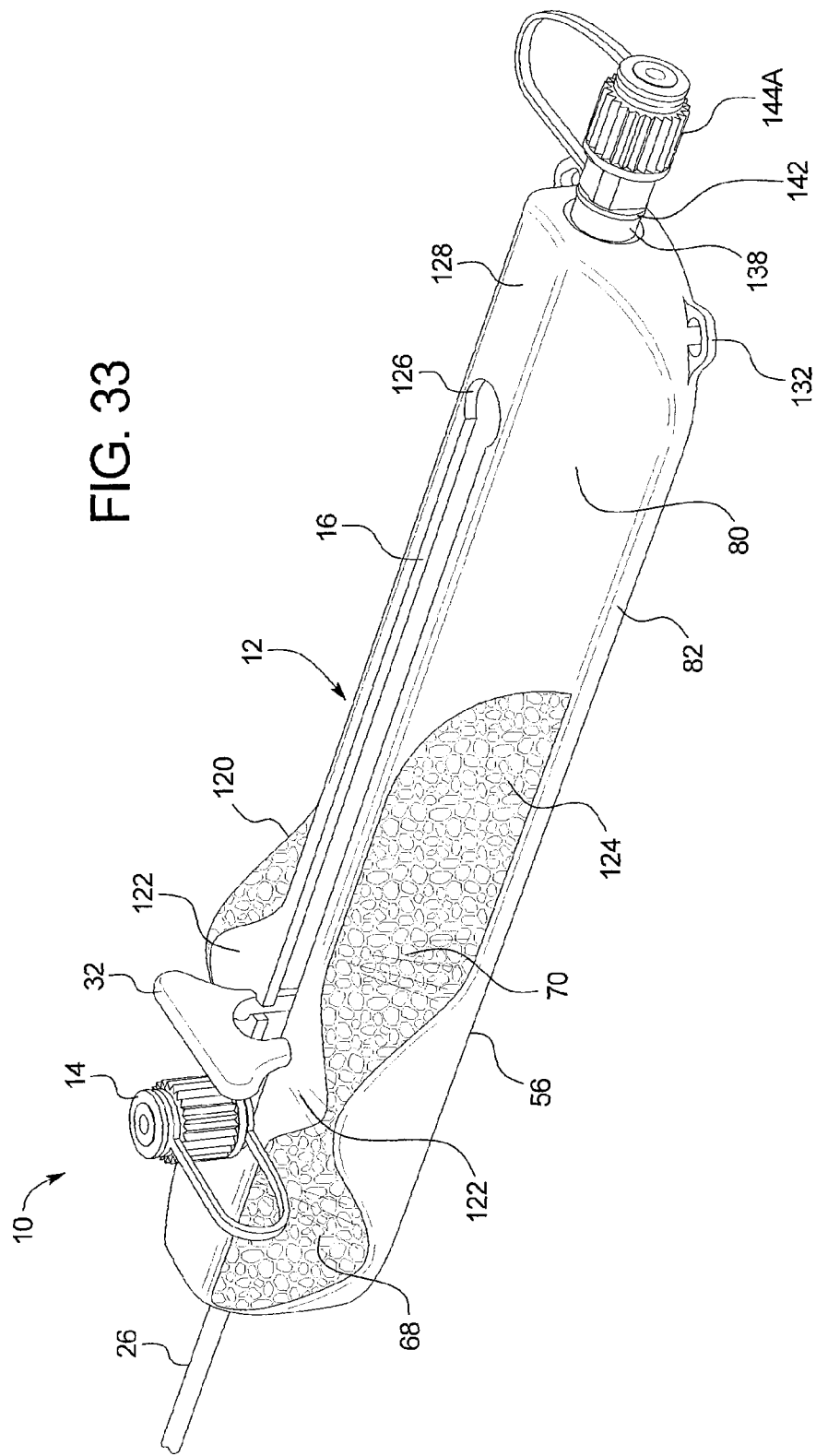
FIG. 33 is a perspective view of another embodiment of the delivery system.

Another embodiment of the delivery system 10 and handle assembly 12 is shown in FIGS. 33-39. The delivery system 10 in FIGS. 33-39 is similar to the delivery system 10 described above. Therefore, it is unnecessary to repeat the description above for every feature of the delivery system 10 of FIGS. 33-39. As shown in FIG. 33-34, the housing 120 need not be provided with the second finger recesses 69 on the bottom side 56 of the housing 120. Instead, the bottom side 56 of the housing 120 may be entirely flat. Thus, in this embodiment, the third finger recesses 70 described above may be referred to as second finger recesses 70. Like the embodiment shown in FIG. 1 (73), the embodiment of FIG. 33 may have a raised flat portion 122 between the first and second finger recesses 68, 70. The raised flat portions 122 may be generally contiguous with the central portion 78 of the housing 120. Texturing 124 may also be provided on the top surface of the housing 120 on opposite sides of the slot 16 along the first and second finger recesses 68, 70 and sloped surfaces 80 if desired. Preferably, the texturing 124 is molded directly into the outer surface of the top housing 150. Unlike the embodiment described above, the embodiment of FIGS. 33-38 need not have a soft elastomer 62 along the edges of the housing 120. Instead, the side surfaces 82 may be made of the same rigid material that the housing 120 is made of. Thus, in this embodiment the height of the side surfaces 82 is preferably about 0.090" to about 0.25".

As shown in FIG. 33, the slot 16 may have a narrower width along substantially the entire length of the slot 16 and an opening 126 at one end, such as the proximal end, that has a wider width. As shown in FIG. 26, the luer fitting 88 of the slide 38 may have an extension 128 with a first width and a coupling end 130 with a second width. The width of the slot 16 may be sized approximately equal to the first width of the extension 128 to minimize the width of the slot 16 and/or so that the edges of the slot 16 provide guide surfaces for the slide 38. However, in order to assemble the slide 38 and the housing 120 together, the width of the opening 126 is sized approximately equal to the second width of the coupling end 130 so that the coupling end 130 can be inserted through the opening 126. After inserting the coupling end 130 through the opening 126, the cap 46 can be connected to the coupling end 130, which may serve as the knob 14.

As shown in FIGS. 33 and 36-38, the handle assembly 12 may also be provided with suture loops 132 at the proximal end of the housing 120 on opposing sides. The suture loops 132 may be useful to secure the handle assembly 12 to a patient's body by sewing sutures through the patient's skin and the suture loops 132. This may be particularly useful where the delivery system 10 is used with a temporary medical device connected to the inner catheter 22 that is intended to be released and maintained in a patient's body for a period of time and then is removed from the patient's body after the period of treatment. Thus, during the period of treatment the delivery system 10 can be secured to the patient's body to ensure that the temporary medical device does not move during the treatment period.

As shown in FIG. 39, the housing 120 may also be provided with a connector 134 at the distal end of the housing 120. Although the connector 134 may be formed as a part of the distal hub 140 described below, the connector 134 may also be an integral feature of the housing 120. The connector 134 may be provided with a series of flexible circumferential ribs 136 adapted to be connected to different types of hubs. This may be particularly useful when the delivery device is used with a temporary medical device like described above in an emergency trauma situation. In such situations, it may be desirable to snap the distal end of the housing 120 into the hub of an introducer catheter or the like. However, in an emergency trauma situation, there may not be sufficient time to select an introduction catheter and delivery system combination with matching connectors and/or emergency personnel may have a limited selection of devices to use. Thus, in this setting it may be desirable for the delivery system 10 handle assembly 12 to have a more universal connector 134 that can connect to different hubs without needing to be concerned with matching single-purpose connectors. Thus, as shown in FIG. 39, the connector 134 may have three different flexible ribs 136A,B,C, with the smallest diameter rib 136A being most distal and the largest diameter rib 136C being most proximal.

As shown in FIG. 34, the handle assembly 12 may be provided with proximal and distal hubs 138, 140 that are separate from the housing 120 but are entrapped within the housing 120. The outer sheath 26 and inner catheter 22 extend through a hole in the distal hub 140, and the inner catheter 22 (and cannula 92 if used) extends through a hole in the proximal hub 138. Separate hubs 138, 140 may be useful to make the handle assembly 12 more adaptable so that different hubs 138, 140 can be assembled into the handle assembly 12 during manufacturing depending on the particular design that is desired for the handle assembly 12. For example, the distal hub 140 may be provided with the connector 134 shown in FIG. 39 if the handle assembly 12 is intended for a temporary medical device in an emergency trauma setting. Alternatively, the distal hub 140 may be provided without connecting features 136 as shown in FIG. 34 if a connector 134 is not needed. The proximal hub 138 is preferably provided with a threaded proximal port 142 that is in communication with an inner lumen of the inner catheter 22. Various types of fittings 144 may be threaded into the proximal hub 138 as desired. For example, as shown in FIG. 33, a fitting 144A with a luer fitting and a cap may be threaded into the proximal hub 138. Alternatively, as shown in FIG. 34, a hemostatic valve 144B with a side fluid port may be threaded into the proximal hub 138. As shown in FIG. 34, the proximal and distal hubs 138, 140 preferably have a series of longitudinal ribs 146 on the circumference of each hub 138, 140. As shown in FIGS. 37-38, the ribs 146 (shown in FIG. 34) engage recesses 148 in the bottom housing 152 and corresponding recesses 148 in the top housing 150. Thus, the proximal and distal hubs 138, 140 are prevented from rotating relative to the housing 120. The entrapment of the proximal and distal hubs 138, 140 within the housing 120 may be accomplished by using the two-piece housing 120 shown in FIGS. 34-35, where the top and bottom housings 150, 152 are clamped together to sandwich the proximal and distal hubs 138, 140 between the top and bottom housings 150, 152. In addition, the proximal and distal hubs 138, 140 may be longitudinally restrained in the housing 120 by providing molded structures in the housing 120 that wrap around portions of the proximal and distal hubs 138, 140. If desired, the proximal and distal hubs 138, 140 may be identical to each other as shown in FIG. 34, with both hubs 138, 140 facing in the same direction.

As shown in FIGS. 34-35, the housing 120 may be a two-piece housing 120 made up of a top housing 150 and a bottom housing 152. The top and bottom housings 150, 152 may be connected together with a series of sockets 154 and pins 156 that engage each other to hold the top and bottom housings 150, 152 together. For example, the top housing 150 may have sockets 154 that extend down from the bottom side of the top housing 150. Each of the sockets 154 have a hole that extends through each socket 154. The bottom housing 152 may have pins 156 that extend up from the top side of the bottom housing 152. The pins 156 may have a non-round cross-section, such as a "+" cross-section. Preferably, the pins 156 are sized to have an interference fit with the holes of the sockets 154 so that when the pins 156 are pushed into the sockets 154, the interference fit holds the top and bottom housings 150, 152 together without any other securement.

As shown in FIG. 34, the bottom housing 152 may be provided with support ribs 158 that extend up from the top side of the bottom housing 152. The support ribs 158 are designed to extend through the open space inside the housing 120 and contact or come close to the bottom side of the top housing 150. This provides support for the top and bottom housings 150, 152 to prevent flexing of the housing 120. Preferably, the support ribs 158A are angled to match the sloped surfaces 80 of the housing 120, but non-angled support ribs 158B may also be provided for non-sloped portions of the housing 120. In addition, the support ribs may be provided on the top housing 150 instead of the bottom housing 152 if desired.

In contrast to the embodiment shown in FIG. 14, where the bottom side 56 is partially defined by the housing 18 and partially defined by the bottom cover 36, the bottom housing 152 in FIG. 34 may form the entire bottom side of the housing 120. In particular, the sides of the top housing 150 contact the top of the bottom housing 152 without wrapping around the edges of the bottom housing 152 to form part of the bottom side 56.

As shown in FIG. 34, the slide 38 may be provided with lateral projections 160 that extend out from the main body 162 of the slide 38. While the indicator tabs 114 described above are also lateral projections, the lateral projections 160 do not need to serve as visual indicators as described above. Instead, the lateral projections 160 in FIG. 34 are used only for lateral stability to prevent the slide 38 from rotating in the housing 120 and to ensure that the slide 38 moves smoothly along the slot 16. Thus, when the slide 38 is assembled into the housing 120 the lateral projections 160 are located within longitudinal recesses in the housing 120. The longitudinal recesses may be defined by a gap between the raised ribs 164 on the bottom housing 152 and top housing 150 when the housings 150, 152 are pressed together.

As shown in FIGS. 36-38, the bottom housing 152 may also be provided with longitudinal ribs 166 between the larger longitudinal ribs 164 that form the gaps for the lateral projections 160. The smaller longitudinal ribs 166 are designed to contact or come close to the bottom of the main body 162 of the slide 38 to further guide the slide 38 and ensure smooth movement of the slide 38. If desired, the ribs 166 may have angled top surfaces to provide improved contact with the round outer surface of the main body 162.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A delivery system for a self-expanding medical device, comprising:
    an inner catheter with a retention surface adapted to longitudinally restrain a self-expanding medical device;
    an outer sheath adapted to extend over said self-expanding medical device to radially restrain said self-expanding medical device in a compressed state;
    a housing connected to said inner catheter, said housing comprising a top side and a bottom side, said top side comprising a top surface having a longitudinal slot extending therethrough, and said bottom side comprising a generally flat surface, wherein a ratio between a width of said flat surface of said bottom side and a height between said bottom side and said top side is about 2.5:1 to about 3.5:1, wherein the top side comprises two opposing first finger recesses disposed above said flat surface of said bottom side, and wherein said two opposing first finger recesses have an upward-facing aspect and are adapted to receive a user's fingers for urging said bottom side of said housing against a patient's body;
    a slide disposed within said housing and being connected to said outer sheath; and
    a knob connected to said slide and extending out of said housing through said slot in said housing, the knob being movable from a proximal end of the slot to a distal end of the slot, wherein said first finger recesses each have a nadir disposed distally from said knob when said knob is positioned at a distal terminal end of said slot;
    wherein said self-expanding medical device is released at a treatment site by longitudinally restraining said housing with respect to said treatment site and moving said knob longitudinally away from said treatment site within said slot of said housing, said outer sheath thereby being withdrawn from said self-expanding medical device while said inner catheter maintains said self-expanding medical device at said treatment site.

2. The delivery system according to claim 1, wherein said ratio is about 3:1.

3. The delivery system according to claim 1, wherein said bottom side is entirely flat.

4. The delivery system according to claim 1, wherein said top side comprises a central longitudinal portion defining said height and opposing sloped surfaces extending downward from said central portion within an angular range of about 30° to about 60°.

5. The delivery system according to claim 1, wherein said slide comprises a fitting extending through said slot, said fitting comprising an extension with a first width approximately equal to a width of said slot along substantially an entire length of said slot, and a coupling end with a second width larger than said width of said slot, said slot comprising an opening with a width approximately equal to said coupling end, wherein said slide and said housing are assemblable by inserting said coupling end through said opening and connecting said knob to said coupling end.

6. The delivery system according to claim 1, wherein said inner catheter extends longitudinally through said housing to a proximal end of said housing, a hub separate from said housing being in communication with a lumen through said inner catheter, said hub being entrapped within said housing and comprising an external port.

7. The delivery system according to claim 1, wherein said housing comprises a connector at a distal end thereof, said connector having a ribs being adapted to connect to a hub of an introducer catheter.

8. The delivery system according to claim 1, wherein said slide comprises a lateral projection disposed within a longitudinal recess in said housing.

9. The delivery system according to claim 1, wherein said housing comprises a top housing and a bottom housing, said bottom housing forming an entirety of said bottom side.

10. The delivery system according to claim 1, wherein said housing comprises a suture loop adapted to attach said housing to a patient's body with a suture.

11. The delivery system according to claim 1, wherein said housing comprises a top housing and a bottom housing, said bottom housing forming an entirety of said bottom side, said slide comprises a lateral projection disposed within a longitudinal recess in said housing between said top and bottom housings, said slide comprises a fitting extending through said slot, said fitting comprising an extension with a first width approximately equal to a width of said slot along substantially an entire length of said slot, and a coupling end with a second width larger than said width of said slot, said slot comprising an opening with a width approximately equal to said coupling end, wherein said slide and said housing are assemblable by inserting said coupling end through said opening and connecting said knob to said coupling end, and said top side comprises a central longitudinal portion defining said height and opposing sloped surfaces extending downward from said central portion within an angular range of about 30° to about 60°.

12. The delivery system according to claim 4, wherein said housing comprises opposing side surfaces that are rigid and about 0.090" to about 0.25" in height.

13. The delivery system according to claim 4, comprising an indicator window extending through at least one of said sloped surfaces, said housing comprising a colored portion viewable through said indicator window, and said slide comprising a slidable colored portion with a different color, wherein said slidable colored portion is viewable through said indicator window when said slide has reached a predetermined location and thereby blocks said colored portion of said housing.

14. The delivery system according to claim 7, wherein said connector comprises three flexible ribs, each of the three flexible ribs having different diameters.

15. A delivery system for a self-expanding medical device, comprising:
   an inner catheter with a retention surface adapted to longitudinally restrain a self-expanding medical device;
   an outer sheath adapted to extend over said self-expanding medical device to radially restrain said self-expanding medical device in a compressed state;
   a housing connected to said inner catheter, said housing comprising a top side and a bottom side, said top side comprising a top surface having a longitudinal slot extending therethrough, and said bottom side comprising a generally flat surface, wherein a ratio between a width of said flat surface of said bottom side and a height between said bottom side and said top side is about 2.5:1 to about 3.5:1, and wherein the top side comprises two opposing first finger recesses disposed distally beyond a distal terminal end of the slot above said flat surface of said bottom side, two opposing second finger recesses along said top side proximal from said first finger recesses, and a raised flat portion being disposed between said first and second finger recesses, wherein said two opposing first finger recesses are upwardly-inclined and are adapted to receive a user's fingers for urging said bottom side of said housing against a patient's body;
   a slide disposed within said housing and being connected to said outer sheath; and
   a knob connected to said slide and extending out of said housing through said slot in said housing;
   wherein said self-expanding medical device is released at a treatment site by longitudinally restraining said housing with respect to said treatment site and moving said knob longitudinally away from said treatment site within said slot of said housing, said outer sheath thereby being withdrawn from said self-expanding medical device while said inner catheter maintains said self-expanding medical device at said treatment site.

16. The delivery system according to claim 15, wherein said top side comprises a central longitudinal portion defining said height and opposing sloped surfaces extending downward from said central portion within an angular range of about 30° to about 60°.

17. The delivery system according to claim 16, wherein said bottom side is entirely flat.

18. The delivery system according to claim 17, wherein said ratio is about 3:1.

19. A delivery system for a self-expanding medical device, comprising:
   an inner catheter with a retention surface adapted to longitudinally restrain a self-expanding medical device;
   an outer sheath adapted to extend over said self-expanding medical device to radially restrain said self-expanding medical device in a compressed state;
   a housing connected to said inner catheter, said housing comprising a top side and a bottom side, said top side comprising a top surface having a longitudinal slot extending therethrough, and said bottom side comprising two opposable bottom recesses separated by a generally flat surface, wherein a ratio between a width of said flat surface of said bottom side and a height between said bottom side and said top side is about 2.5:1 to about 3.5:1, and wherein the top side comprises two opposing first finger recesses disposed above said flat surface of said bottom side, wherein said two opposing first finger recesses have an upward-facing aspect and are adapted to receive a user's fingers onto the top surface for urging said bottom side of said housing against a patient's body, and extend distally beyond a distal terminal end of the slot in the housing:

a slide disposed within said housing and being connected to said outer sheath; and a knob connected to said slide and extending out of said housing through said slot in said housing, wherein said first finger recesses are disposed distally from said knob when said knob is adjacent a distal end of said slot; and wherein the knob comprises a port situated out of said housing, wherein the port is in fluid communication with an annular space inside the outer sheath;

wherein said self-expanding medical device is released at a treatment site by longitudinally restraining said housing with respect to said treatment site and moving said knob longitudinally away from said treatment site within said slot of said housing, said outer sheath thereby being withdrawn from said self-expanding medical device while said inner catheter maintains said self-expanding medical device at said treatment site.

20. The delivery system according to claim 19, wherein the knob further comprises a cap and a luer fitting, wherein the cap may be coupled to the luer fitting to seal said port.

* * * * *